US00PP08253P

United States Patent [19]

Klemm

[11] Patent Number: Plant 8,253

[45] Date of Patent: Jun. 8, 1993

[54] GERANIUM PLANT NAMED KLEDEDIL

[75] Inventor: Siegfried Klemm, Stuttgart, Fed. Rep. of Germany

[73] Assignee: Klemm & Sohn, Stuttgart, Fed. Rep. of Germany

[21] Appl. No.: 804,050

[22] Filed: Dec. 9, 1991

[51] Int. Cl.[5] ..... A01H 5/00
[52] U.S. Cl. ..... Plt./87.12
[58] Field of Search ..... Plt./87.12

*Primary Examiner*—James R. Feyrer
*Attorney, Agent, or Firm*—Tilton, Fallon, Lungmus & Chestnut

[57] ABSTRACT

A new and distinctive Ivy Geranium variety particularly distinguished by its pleasing purple violet flowers which are produced profusely in medium size round clusters. The clusters are borne on strong stalks and contrast nicely with the green foilage.

1 Drawing Sheet

BACKGROUND OF THE PLANT

A new geranium plant was originated as a chance seedling from seed collected in mass from a collection of unidentified ivy geranium plants maintained as a germ plasm pool in open pollination in our nursery in Stuttgart. The instant plant is believed to be a hybrid by its characteristic of medium vigor, good rooted character, ample stem strength and desirable habit, and because of the double aaspect of the flowers, not usually seen in plants of this market class and by the pleasing flower characteristics of color and quality. This seedling blossomed for the first time in 1986 and because of its good rooting character and its pleasing purple violet flower color, this seedling was selected for propagation which was done by me and under my direction at Stuttgart by means of cuttings. Successive generations of this plant have shown that its novel and distinguishing characteristics are fixed and its homogeneity holds true from generation to generation.

DESCRIPTION OF THE DRAWING

This new ivy geranium cultivar is illustrated by the accompanying photographic drawing which shows a fully developed plant with several clusters of flowers and buds in various stages of development which illustrate their form and the pleasing color contrast between the purple violet flowers and the green foilage. The color rendition is as nearly true to that herein specified as is reasonably possible to obtain by conventional photographic procedures.

DESCRIPTION OF THE PLANT

The following is aa detailed description of my new ivy geranium variety as observed of plants grown both in greenhouses in outdoors at Stuttgart, with color designation according to the R.H.S. Colour Chart published by The Royal Horticultural Society of London, England.

THE PLANT

Origin: Seedling.
Parentage:
*Seed parent.*—Unknown.
*Pollen parent.*—Unknown. Both the seed and pollen parent are from the breeding stock maintained in our nursery in Stuttgart.
Classiciation:

*Botanic.*—Pellargonium peltatum hydrid.
*Commercial.*—Ivy Geranium.
Form: Bushy cascade of ivy geranium.
Height: about 18 cm.
Growing rate: The rooted cuttings of the ivy geranium are potted in the middle of January and pinched in six weeks and all early buds and flowers are taken until March 15 and then they are left to come to flower evenly. In April the precocity is recognized. The growth rate is thus medium fast compared to other ivy varieties. The internode length varies from 1 to 2.5 cm.
Branching character: Good self branching.
*Cluster stems.*—8 to 10 cm.
*Main stem.*—Between 28 and 25 cm.
Growth habit: Fast rooting.
*Form.*—Horizontal and dropping, with good strength.
Foliage:
*Quantity.*—Medium.
*Size of leaf.*—Length — 7-9 cm. Width — 5 cm.
*Shape.*—Ivy shaped.
*Margins.*—Entire.
*Texture.*—Leathery.
*Color.*—Upper side — medium green RHS 147A. Under side — light green RHS 146A.
*Veins.*—5 main veins.
*Petioles of leaves.*—Length — between 3 and 3.3 cm.

THE BUD

Size: Large.
*Diameter.*—Between 1 and 2 cm.
*Length.*—Approximately 1.5 cm.
*Shape.*—Ovoid and pointed.
*Opening Rate.*—Medium.
Color of petals:
*When sepals first open.*—Purple violet.
*When petals begin to unfurl.*—Violet.
Sepals:
*Number.*—5.
*Shape.*—Ovoid and pointed.
*Character.*—The sepals stand up when the flower opens.
*Color.*—Green.
Cluster stem:

*Length.*—Between 8 and 10 cm. A full blooming cluster taken between the months May to September.

*Strength.*—Rigid.

*Color.*—Green.

INFLORESCENCE

Blooming Habit: Continuous and profuse from Spring to late Fall. Self pinching, even with the formation of seed.

Size of cluster:

*Diameter.*—About 5.5 cm.

*Depth.*—About 0.8 cm.

*Borne.*—As a medium sized cluster on an upright stalk.

Flowers:

*Number.*—A full blooming cluster has a diameter of 7 to 7.5 cm. It is built by 7 to 9 florets with a diameter of 5.5 cm with 20 to 24 petals. The blooming cluster keeps fresh and lovely on the plant about 12 to 14 days after the first floret opens. More specifically, the clusters have between 7 to 9 florets in the summer 5 to 7 in the winter in the green house under lamps. The shape of the flower is a filled cup because of the 20 and more petals. This makes the flower of 'Klededil' very distinctive.

*Form.*—Cup-shaped and more flattened as the bloom matures.

Florets:

*Number.*—Between 20 and 24 per floret. Shape: The florets have rather short stems and stand hemispherically around the green cluster stem. Fullness: Very full. They appear profusely on the dark green leaved plant and show a great contrast between the deep violet flower color and the leaf color.

*Size.*—5.5 cm in diameter.

*Florets.*—7 to 9 florets in a cluster.

*Arrangement.*—Imbricated.

*Form.*—Broad with entire margins.

*Apex.*—Round and entire.

*Color.*—The florets are perfect containing both pistils and stamens. Both outer and inside petals. 80-B on the body and base. 82-C on the reverse side.

Floret stems: Length approximately 2 cm. Color — Medium green. Strength — Very strong.

Character: Flowers stand hemispherically around the stem of the cluster.

Discoloration after full bloom: No discoloration.

THE REPRODUCTIVE ORGANS

Stamens:

*Number.*—7.

*Arrangement*—They are standing in a circle around the ovaries.

Anthers:

*Size.*—Approximately 2 mm.

*Color.*—Orange

Filaments:

*Length.*—Approximately 4 mm.

*Color.*—Pink.

Pollen:

*Color.*—Orange.

Pistils:

*Number.*—1.

Styles: Length — approximately 1.1 cm.

*Color.*—Green and pink.

Stigmas:

*Color.*—Light violet.

Characteristics of the ovaries: Big and green.

Fruit: The fruit is fertile.

*Shape.*—Ovoid.

*Color at Maturity.*—Brown.

The purple violet flowers of this geranium are more purple than those of the plant Amethyst (unpatented). Also, the cuttings root one week earlier than those of Amethyst. The plant is bigger and it grows stronger.

I claim:

1. The new and distinctive ivy geranium variety, substantially as herein shown and described, characterized by its purple violet flowers, its contrasting foilage and its fast-rooting character.

* * * * *

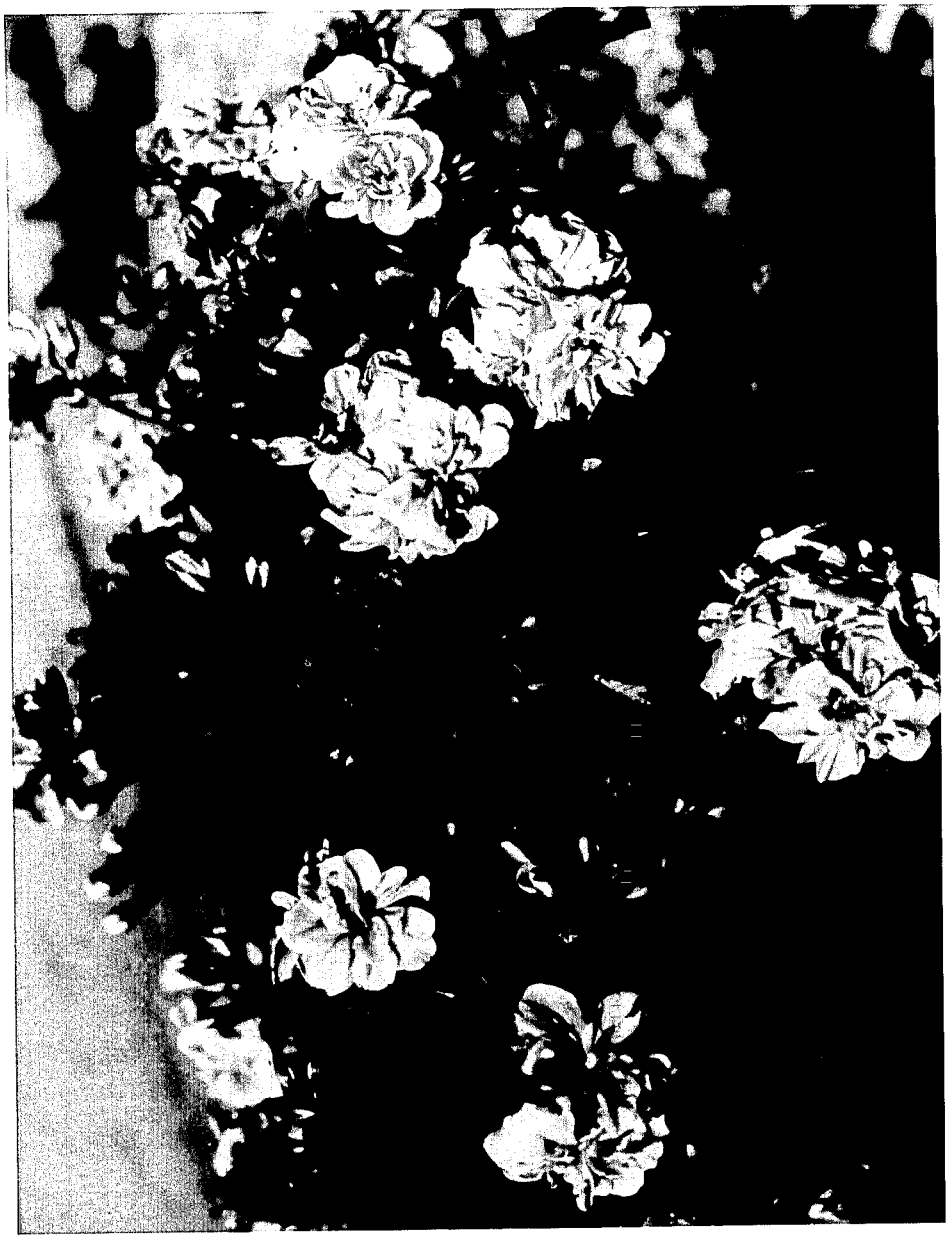

UNITED STATES PATENT AND TRADEMARK OFFICE

CERTIFICATE OF CORRECTION

PATENT NO. : PP 08,253

DATED : Jun. 8, 1993

INVENTOR(S) : Klemm

It is certified that error appears in the above-identified patent and that said Letters Patent is hereby corrected as shown below:

Column 1, line 10, delete "aaspect" and insert --aspect--; line 34, delete "aa" and insert --a--; line 48, delete "classiciation" and insert --classification--.

Signed and Sealed this

Fifteenth Day of March, 1994

*Attest:*

*Attesting Officer*

Bruce Lehman

BRUCE LEHMAN

*Commissioner of Patents and Trademarks*